United States Patent
Chen et al.

(10) Patent No.: US 11,821,018 B2
(45) Date of Patent: Nov. 21, 2023

(54) METHODS FOR CELL-FREE PROTEIN EXPRESSION

(71) Applicant: Nuclera Ltd, Cambridge (GB)

(72) Inventors: Michael Chun Hao Chen, Cambridge (GB); Sihong Chen, Cambridge (CA); Christopher Dulson, Cambridge (GB); Sumit Kalsi, Cambridge (GB); Gordon Ross McInroy, Cambridge (GB); Stephanie Reikine, Cambridge (GB)

(73) Assignee: Nuclera Ltd., Cambridge (GB)

( * ) Notice: Subject to any disclaimer, the term of this patent is extended or adjusted under 35 U.S.C. 154(b) by 0 days.

(21) Appl. No.: 17/969,323

(22) Filed: Oct. 19, 2022

(65) Prior Publication Data

US 2023/0042211 A1 Feb. 9, 2023

Related U.S. Application Data

(63) Continuation of application No. 17/799,323, filed as application No. PCT/GB2021/050362 on Feb. 15, 2021.

(30) Foreign Application Priority Data

Feb. 14, 2020 (GB) .................................. 2002077

(51) Int. Cl.
*C12P 21/02* (2006.01)
*B01L 3/00* (2006.01)
*C12M 3/06* (2006.01)
*C07K 14/435* (2006.01)

(52) U.S. Cl.
CPC ............ *C12P 21/02* (2013.01); *B01L 3/50273* (2013.01); *C07K 14/43595* (2013.01); *C12M 23/16* (2013.01); *B01L 2200/0673* (2013.01); *B01L 2300/0645* (2013.01); *B01L 2300/0654* (2013.01); *B01L 2400/0427* (2013.01)

(58) Field of Classification Search
CPC ......... B01L 3/50273; B01L 2200/0673; B01L 2400/0427; C12M 23/16
See application file for complete search history.

(56) References Cited

U.S. PATENT DOCUMENTS

| 7,851,184 B2 * | 12/2010 | Pollack | C12Q 1/6869 435/91.2 |
| 2006/0228708 A1 | 10/2006 | Smilansky | |
| 2019/0111433 A1 | 4/2019 | French | |
| 2019/0262829 A1 * | 8/2019 | Umapathi | G02B 26/005 |

FOREIGN PATENT DOCUMENTS

| EP | 1649025 A2 | 4/2006 |
| WO | 2019/153067 A1 | 8/2019 |

OTHER PUBLICATIONS

Fallah-Araghi et al. ("A completely in vitro ultrahigh-throughput droplet-based microfluidic screening system for protein engineering and directed evolution." Lab on a Chip 12.5 (2012): 882-891). (Year: 2012).*
Cho et al. ("Droplet-based microfluidic platform for high-throughput, multi-parameter screening of photosensitizer activity." Analytical chemistry 85.18 (2013): 8866-8872.). (Year: 2013).*
Bansal et al., Axisymmetric and Nonaxisymmetric Oscillations of Sessile Compound Droplets in an Open Digital Microfluidic Platform. Langmuir. Oct. 17, 2017;33(41):11047-11058.
Courtois et al., An integrated device for monitoring time-dependent in vitro expression from single genes in picolitre droplets. Chembiochem. Feb. 15, 2008;9(3):439-46.
Fallah-Araghi et al., A completely in vitro ultrahigh-throughput droplet-based microfluidic screening system for protein engineering and directed evolution. Lab Chip. Mar. 7, 2012;12(5):882-91.
Fowler et al., Enhancement of Mixing by Droplet-Based Microfluidics. Proc IEEE Int Conf MEMS. pp. 97-100, Jan. 2002.
Geng et al., Antifouling digital microfluidics using lubricant infused porous film. Lab Chip. Jun. 25, 2019;19(13):2275-2283.
International Search Report and Written Opinion for Application No. PCT/GB2021/050362, dated May 17, 2021, 8 pages.
U.S. Appl. No. 17/799,323, filed Aug. 12, 2022, Pending.
Avilov et al., Fluorescence protein complementation in microscopy: applications beyond detecting bi-molecular interactions. Methods Appl Fluoresc. Nov. 20, 2018;7(1):012001, 13 pages.
Ayoubi-Joshaghani et al., Cell-free protein synthesis: The transition from batch reactions to minimal cells and microfluidic devices. Biotechnol Bioeng. Apr. 2020;117(4):1204-1229.
Kays, Observation and quantification of protein production in single living cells. Integrated Program in Neuroscience McGill University, Montreal. Thesis, 171 pages, Nov. 2016.
Saeki et al., Microcompartmentalized cell-free protein synthesis in semipermeable microcapsules composed of polyethylenimine-coated alginate. J Biosci Bioeng. Aug. 2014;118(2):199-204.
Xiao et al., Integration of cell-free protein synthesis and purification in one microfluidic chip for on-demand production of recombinant protein. Biomicrofluidics. Sep. 13, 2018;12(5):054102, 13 pages.
International Search Report and Written Opinion for Application No. PCT/GB2021/052140, dated Dec. 1, 2021, 12 pages.

* cited by examiner

*Primary Examiner* — Sahana S Kaup
(74) *Attorney, Agent, or Firm* — McCarter & English, LLP; Yu Lu (57) ABSTRACT

Disclosed is a method for the cell-free expression of peptides or proteins in a liquid filled digital microfluidic device. The droplets having the components required for cell-free protein expression can be manipulated by electrokinesis in order to enhance levels of protein expression in the droplets.

13 Claims, 10 Drawing Sheets

METHODS FOR CELL-FREE PROTEIN EXPRESSION

REFERENCE TO RELATED APPLICATION

This application is a continuation application of U.S. patent application Ser. No. 17/799,323, filed on Aug. 12, 2022 as a U.S. National Stage Application filed under 35 U.S.C. 371, based on International Patent Application No. PCT/GB2021/050362, filed on Feb. 15, 2021, which claims foreign priority to UK Patent Application No. GB 2002077.2, filed on Feb. 14, 2020, the entire contents of each of which, including drawings and any sequence listings, are incorporated herein by reference.

FIELD OF THE INVENTION

Disclosed is a method for the cell-free expression of peptides or proteins in a digital microfluidic device. The droplets having the components required for cell-free protein synthesis (CFPS), otherwise known as in vitro protein synthesis, can be manipulated by electrokinesis in order to effect and improve protein expression.

BACKGROUND OF THE INVENTION

Electrowetting is the modification of the wetting properties of a surface (which is typically hydrophobic) with an applied electric field. Microfluidic devices for manipulating droplets or magnetic beads based on electrowetting have been extensively described. In the case of droplets in channels this can be achieved by causing the droplets, for example in the presence of an immiscible carrier fluid, to travel through a microfluidic channel defined by the walls of a cartridge or microfluidic tubing. Embedded in the walls of the cartridge or tubing are electrodes covered with a dielectric layer each of which are connected to an A/C biasing circuit capable of being switched on and off rapidly at intervals to modify the electrowetting field characteristics of the layer. This gives rise to the ability to steer the droplet along a given path.

As an alternative to microfluidic channel systems, droplets can also be generated and manipulated on planar surfaces using digital microfluidics (DMF). In contrast to channel based microfluidics, DMF utilizes alternating currents on an electrode array for moving fluid on the surface of the array. Liquids can thus be moved on an open-plan device by electrowetting. Digital microfluidics allows precise control over the droplet movements including droplet fusion and separation.

Cell-free protein synthesis, also known as in vitro protein synthesis or CFPS, is the production of peptides or proteins using biological machinery in a cell-free system, that is, without the use of living cells. The in vitro protein synthesis environment is not constrained within a cell wall or limited by conditions necessary to maintain cell viability, and enables the rapid production of any desired protein from a nucleic acid template, usually plasmid DNA or RNA from an in vitro transcription. CFPS has been known for decades, and many commercial systems are available. Cell-free protein synthesis encompasses systems based on crude lysate (*Cold Spring Harb Perspect Biol.* 2016 December; 8(12): a023853) and systems based on reconstituted, purified molecular reagents, such as the PURE system for protein production (*Methods Mol Biol.* 2014; 1118: 275-284). CFPS requires significant concentrations of biomacromolecules, including DNA, RNA, proteins, polysaccharides, molecular crowding agents, and more (*Febs Letters* 2013, 2, 58, 261-268).

Lab Chip, 2012, 12, 882 (entitled A completely in vitro ultrahigh-throughput droplet-based microfluidic screening system for protein engineering and directed evolution) describes a system based on droplets in a flowing capillary channel, not a three-dimensional array based EWOD system.

United States Patent Application 20210016283 describes microwell array systems for high throughput protein expression.

US20160230203A1 entitled a Portable Fluidic Platform For Rapid Cell-Free Production of Protein Biologics describes an integrated fluidic platform encompassing, cell-free protein synthesis systems coupled to rapid protein purification and characterization modules enabling production of protein biologics.

U.S. Ser. No. 10/464,067 describes Air-matrix digital microfluidics (DMF) apparatuses and methods of using them to prevent or limit evaporation and surface fouling of the DMF apparatus. To date, digital microfluidics, electrowetting-on-dielectric (EWoD), and electrokinesis in general have only found limited uses in cell-free biological-based applications, mostly due to biofouling, where biological components such as proteins, nucleic acids, crude cell extracts and other bioproducts adsorb and/or denature to hydrophobic surfaces. Biofouling is well known in the art to limit the ability of EWoD devices to manipulate droplets containing biomacromolecules. Wheeler and colleagues report that the maximum actuation time for droplets on EWoD devices containing biological media is 30 min before biofouling inhibits EWoD-based droplet actuation (*Langmuir* 2011, 27, 13, 8586-8594).

Digital microfluidics can be carried out in an air-filled system where the liquid drops are manipulated on the surface in air. However, at elevated temperatures or over prolonged periods, the volatile aqueous droplets simply dry onto the surface by evaporation. This issue is compounded by the high surface area to volume ratio of nanoliter and microliter sized drops. Hence air-filled systems are generally not suitable for protein expression where the temperature of the system needs to be maintained at a temperature suitable for enzyme activity and the duration of the synthesis needs to be prolonged for synthesized proteins levels to be detectable.

Protein expression typically requires an ample supply of oxygen. The most convenient and high yielding way to power CFPS is via oxidative phosphorylation where $O_2$ serves as the final electron acceptor; however, there are other ways that involve replenishing with energy molecules not involved in oxidative phosphorylation. In a confined microfluidic or digital microfluidic system of droplets, insufficient oxygen is available to enable efficient protein synthesis.

Due to the limitations described above, the use of cell-free systems and ribosomal extracts on EWoD devices have been limited to conceptual discussions, given that biological processes typically require hours of incubation at a temperature above room temperature to achieve intended results (*Biomicrofluidics* 2013, 7, 014108). Thus whilst there are suggestions in the prior art as to the desirability of performing CPFS in microfluidic devices, a practical working system has never been demonstrated.

SUMMARY OF THE INVENTION

Described herein are improved methods allowing for the cell-free expression of peptides or proteins in a digital microfluidic device. Included is a method for the cell-free expression of peptides or proteins in a microfluidic device wherein the method comprises one or more droplets containing a nucleic acid template (i.e., DNA or RNA) and a cell-free system having components for protein expression in an oil-filled environment, and moving said droplets using electrokinesis. The components for the cell-free protein synthesis droplet can be pre-mixed prior to introduction to or mixed on the digital microfluidic device.

The droplet can be repeatedly moved for at least a period of 30 minutes whilst the protein is expressed. The droplet can be repeatedly moved for at least a period of two hours whilst the protein is expressed. The droplet can be repeatedly moved for at least a period of twelve hours whilst the protein is expressed. The act of moving the droplet allows oxygen to be supplied to the droplet and dispersed throughout the droplet. The act of moving improves the level of protein expression over a droplet which remains static.

The droplet can be moved using any means of electrokinesis. The droplet can be moved using electrowetting-on-dielectric (EWoD). The electrical signal on the EWoD or optical EWoD device can be delivered through segmented electrodes, active-matrix thin-film transistors, or digital micromirrors.

The oil in the device can be any water immiscible liquid. The oil can be mineral oil, silicone oil, an alkyl-based solvent such as decane or dodecane, or a fluorinated oil. The oil can be oxygenated prior to or during the expression process. Alternatively, the device can be an air-filled device where droplets containing cell-free protein synthesis reagents are rapidly moved into position and fixed into an array under a humidified gas to prevent evaporation. Humidification can be achieved by enclosing or sealing the digital microfluidic device and providing on-board reagent reservoirs. Additionally, humidification can be achieved by connecting an aqueous reservoir to an enclosed or sealed digital microfluidic device. The aqueous reservoir can have a defined temperature or solute concentration in order to provide specific relative humidities (e.g., a saturated potassium sulfate solution at 30° C.). Additionally, a liquid wax material can be used to prevent evaporation.

A source of supplemental oxygen can be supplied to the droplets. For example droplets or gas bubbles containing gaseous or dissolved oxygen can be merged with the droplets during the protein expression. Additionally, a source of supplemental oxygen can be found by oxygenating the oil that is used as the filler medium. It is well-known in the art that oils such as hexadecane, HFE-7500, and others can be oxygenated to support the oxygen requirements of cell growth, especially *E. coli* cell growth (*RSC Adv.*, 2017, 7, 40990-40995). Oxygenation can be achieved by aerating the oil with pure oxygen or atmospheric air.

The droplets can be formed before entering the microfluidic device and flowed into the device. Alternatively the droplets can be merged on the device. Included is a method comprising merging a first droplet containing a nucleic acid template such as a plasmid with a second droplet containing a cell-free extract having the components for protein expression to form a combined droplet capable of cell-free protein synthesis.

The droplets can be split on the device either before or after expression. Included herein is a method further comprising splitting the aqueous droplet into multiple droplets. If desired the split droplets can be screened with further additives. Included is a method wherein one or more of the split droplets are merged with additive droplets for screening.

Included herein are kits for performing the method.

Disclosed herein is a kit for preparing a plurality of peptide or proteins comprising
a. a digital microfluidic device;
b. a reagent source to generate a plurality of droplets containing a cell-free system having the components for protein expression; and
c. an oil, optionally mineral oil, silicone oil, an alkyl-based solvent such as decane or dodecane, or a fluorinated oil, which can be optionally oxygenated.

FIGURES

FIG. 1. General schematic of electrowetting-on-dielectric (EWoD) enabled cell-free protein synthesis (CFPS). (top) A and B represent reagent droplets necessary for CFPS. In one embodiment, A is an aqueous droplet ribosomal extract or cell-free protein synthesis master mix and B is an aqueous droplet containing DNA encoding for gene to be expressed into protein. C represents a filler medium that surrounds the aqueous droplet. In one embodiment, C is atmospheric air. In another embodiment, C is an oil or oxygenated oil, such as dodecane oil, mineral oil, or silicone oil. (middle) When an electrode is switched "ON" as indicated by the switch elements below the electrodes, an electrowetting force is applied to the droplet. The arrows indicate EWoD force imparting droplet actuation by virtue of voltage applied from indicated addressable electrode. (bottom) A+B indicate mixing by EWoD of droplets A and B to effect CFPS.

FIG. 2. mmCherry protein was expressed through CFPS in a 96-well PCR plate. The mmCherry gene contained within a p70a vector was combined with the Sigma 70 Master Mix containing 0.1% v/v Tween 20 to a final concentration of 5 nanomolar plasmid. The combined CFPS solution was then incubated at 29° C. with an air permeable membrane. At the indicated timepoints, mmCherry expression was monitored by measuring total fluorescence intensity of the combined CFPS solution. Fluorescence was monitored with an excitation wavelength of 532 nm and an emission wavelength of 610 nm. Maximum fluorescence was achieved over a 24 h timeframe.

FIG. 3. mmCherry protein was expressed through CFPS on an EWoD device. (top) Plasmid containing the mmCherry gene was premixed with the cell-free extract off chip and rapidly side-ported onto the EWoD device. Several droplets were created from the side-ported combined droplet: (top-A) actuated and mixed for the indicated amount of time; (top-B) actuated in position for the indicated amount of time; and (top-C) not actuated or mixed. Fluorescence was monitored with an excitation wavelength of 545 nm and an emission wavelength at 605 nm with a filter set from Chroma Technology Corp. (USA). Electrowetting-on-dielectric (EWoD) droplet actuation was performed on instrumentation supplied by Sci-Bots Inc. (CAN). EWoD droplet actuation was performed in a dodecane filler medium at 30° C. myTXTL Sigma 70 Master Mix and pTXTL-P70a-mmCherry plasmid (Arbor Biosciences Corp., USA) were used according to manufacturer instructions to express mmCherry red fluorescent protein. (bottom) Plasmid containing the mmCherry gene was introduced to the cell-free extract on the device, and the combined droplet (white arrow D) was mixed via EWoD actuation for the indicated amount of time. FIG. 3 demonstrates that CFPS reagents can be moved by electrokinetic actuation to effect CFPS on an EWoD device. Expression of proteins in CFPS systems occurs at similar kinetics and absolute intensities when comparing CFPS in 96-well plates versus CFPS in an EWoD device (FIGS. 2 and 3). FIG. 3 (bottom) demonstrates that a separate plasmid droplet can be merged via EWoD actuation into a cell-free extract, and the combined droplet can be mixed and actuated for hours to effect CFPS. This long-term actuation of CFPS droplets is surprising as it is well-known in the art that EWoD devices are sensitive to a phenomenon known as bio-fouling, which prevents EWoD actuation.

FIG. 4. Setting up cell-free protein synthesis on a digital microfluidic device with pre-mixed nucleic acid template. Multiple cell-free protein synthesis (CFPS) droplets were split (actuation right to left) from a series of interstitial reagent reservoirs (arrows) on an active-matrix EWOD droplet actuator device. The solution in the interstitial reagent reservoir contains a plasmid encoding for mCherry fluorescent protein (5 nM), reagents necessary to perform cell-free protein synthesis, and Tween-20 (0.1% v/v). The figure shows snapshots of a video demonstrating the splitting of droplets containing a plasmid encoding for mCherry (5 nM), CFPS mastermix (Arbor Bioscience), and Tween-20 (0.1% v/v) on the device. Scale bar is 20 mm. Droplets of size 1.2 mm$^2$ were requested from the interstitial reagent reservoirs. Video snapshots (1)-(4) move forward in time.

FIG. 5. Expression of mCherry fluorescent protein through cell-free protein synthesis on a digital microfluidic device. The fluorescent protein was expressed after droplets containing all reagents necessary for cell-free protein synthesis of the fluorescent protein including plasmid were split from a series of interstitial reagent reservoirs (arrows) on an active-matrix EWOD droplet actuator device. The solution in the interstitial reagent reservoir contains a plasmid encoding for mCherry fluorescent protein (5 nM), reagents necessary to perform cell-free protein synthesis, and Tween-20 (0.1% v/v). After splitting the reservoir into smaller droplets (actuation right to left) from an interstitial reagent reservoir (right) on an active-matrix EWOD droplet actuator device, the split droplets were incubated on the device for the times indicated below. The figure shows snapshots of a video demonstrating the splitting of droplet containing a plasmid encoding for mCherry (5 nM), CFPS mastermix (Arbor Bioscience), and Tween-20 (0.1% v/v) on the device. Scale bar is 20 mm. Droplets of size 1.2 mm$^2$ were requested from the interstitial reagent reservoirs. Video snapshots correspond with time as follows: (1) t=0, (2) t=15 mins, (3) t=55 mins (4) t=4.5 hr. The sample was incubated in a room set to 29° C. Images were acquired using Canon EOS 5D Mark III and an acquisition time of 1 second.

For FIGS. 4-5, images were acquired as described in FIG. 3.

FIG. 10 depicts a conventional electrowetting device with a substrate 10 and a plurality of individually controllable elements 11. The individually controllable elements may be arranged in an array such that multiple droplets may be manipulated simultaneously. The electrical properties of the individually controllable elements 11 can be varied. For example, each individually controllable element may comprises an electrode or a circuit. As shown in FIG. 10 each individually controllable element is connected to a voltage source. Alternatively, each element may comprise a thin film semiconductor in which the electrical properties can be modulated by incident light or a thin film photoconductor whose properties can be modulated by incident light. Covering the individually controllable elements 11 is a dielectric layer 12. As an alternative to the dielectric layer 12 there may be an insulator. The insulator/dielectric may be made of $SiO_2$, silicon oxynitride, $Si_3N_4$, hafnium oxide, yttrium oxide, lanthanum oxide, titanium dioxide, aluminum oxide, tantalum oxide, hafnium silicate, zirconium oxide, zirconium silicate, barium titanate, lead zirconate titanate, strontium titanate, barium strontium titanate, parylene siloxane, epoxy or a mixture thereof. The insulator/dielectric layer has a thickness of 10-10,000 nm. On top of the insulator 12 (or dielectric) is a hydrophobic coat 13. The hydrophobic coat may comprise a fluoropolymer such as, for example, Teflon, CYTOP or PTFE. The hydrophobic coating layer may be made of an amorphous fluoropolymer or siloxane or organic silane. The hydrophobic layer has a thickness of 1-1,000 nm. A second electrode 14 is positioned opposite the array of individually controllable elements and the second electrode and the individually controllable elements are separated by a spacer 15 which defines an electrokinetic workspace.

FIG. 11 depicts an electrowetting device according to the invention in which, on top of the individually controllable elements is a functional coating comprising three component parts: a dielectric layer 12, a conformal layer 30 and a hydrophobic layer 12. According to an embodiment the conformal coat is made of parylene, or preferably parylene C. The conformal layer 20 has a thickness of 10-10,000 nm and prevents ions from interacting with the insulator/dielectric layer 12. The second electrode 14 may comprise a second hydrophobic layer facing the (first) hydrophobic layer. The electrokinetic workspace is then formed between the hydrophobic layers. In order to promote adhesion between the different layer gaseous precursors are often used. This can be used when the layers are deposited using a spin coating or a dip coating.

FIG. 13 depicts an array of individually controllable elements forming an electrode array 202. FIG. 13 is a diagrammatic view of an exemplary driving system 900 for controlling droplet operation by an AM-EWoD propulsion electrode array 902. The AM-EWoD driving system 900 may be in the form of an integrated circuit adhered to a support plate. The elements of the EWoD device are arranged in the form of a matrix having a plurality of data lines and a plurality of gate lines. Each element of the matrix contains a TFT for controlling the electrode potential of a corresponding electrode, and each TFT is connected to one of the gate lines and one of the data lines. The electrode of the element is indicated as a capacitor Cp. The storage capacitor Cs is arranged in parallel with Cp and is not separately shown in FIG. 13. The controller shown comprises a microcontroller 94 including control logic and switching logic.

It receives input data relating to droplet operations to be performed from the input data lines 92. The microcontroller has an output for each data line of the EWoD matrix, providing a data signal. A data signal line 906 connects each output to a data line of the matrix. The microcontroller also has an output for each gate line of the matrix, providing a gate line selection signal. A gate signal line 98 connects each output to a gate line of the matrix. A data line driver 910 and a gate line driver 912 is arranged in each data and gate signal line, respectively. The figure shows the signals lines only for those data lines and gate lines shown in the figure. The gate line drivers may be integrated in a single integrated circuit. Similarly, the data line drivers may be integrated in a single integrated circuit. The integrated circuit may include the complete gate driver assembly together with the microcontroller. The majority of commercially available gate drivers are based on shift registers and cannot be used for adaptive driving. However, UC8152 (UltraChip Inc., San Jose, California), a 480-channel gate/source programmable driver, includes the unusual capability of selecting any gate lines to be "ON" at any one time, so it may be used to simultaneously drive a plurality of lines. The integrated circuit may be integrated on a support plate of the AM-EWoD device. The integrated circuit may include the entire AM-EWoD device driving system. The data line drivers provide the signal levels corresponding to a droplet operation. The gate line drivers provide the signals for selecting the gate line of which the electrodes are to be actuated. A sequence of voltages of one of the data line drivers 910 is shown in the Figure. As illustrated above, when there is large enough positive voltage on the gate line then there is low impedance between the data line and pixel, so the voltage on the data line is transferred to the pixel. When there is a negative voltage on the TFT gate then the TFT is high impedance and voltage is stored on the pixel capacitor and not affected by the voltage on the data line. If no movement is needed, or if a droplet is meant to move away from a propulsion electrode, then 0 V will be applied to that (non-target) propulsion electrode. If a droplet is meant to move toward a propulsion electrode, an AC voltage will be applied to that (target) propulsion electrode. The figure shows four columns labelled n to n+3 and five rows labelled n to n+4.

As illustrated in FIG. 13, traditional AM-EWoD cells use line-at-a-time addressing, in which one gate line n is high while all the others are low. The signals on all of the data lines are then transferred to all of the pixels in row n. At the end of the line time gate line n signal goes low and the next gate line n+1 goes high, so that data for the next line is transferred to the TFT pixels in row n+1. This continues with all of the gate lines being scanned sequentially so the whole matrix is driven. This is the same method that is used in almost all AM-LCDs, such as mobile phone screens, laptop screens and LC-TVs, whereby TFTs control the voltage maintained across the liquid crystal layer, and in AM-EPDs (electrophoretic displays).

DETAILED DESCRIPTION

Described herein are improved methods allowing for the cell-free expression of peptides or proteins in a digital microfluidic device. Included is a method for the cell-free expression of peptides or proteins in a microfluidic device wherein the method comprises one or more droplets containing nucleic acid templates and a cell-free system having components for protein expression in an oil-filled environment, and moving said droplets using electrokinesis.

The methods described herein allow matrix screening with small volumes of an expensive reagent in order to enable wider use of cell-free lysates and ribosomal extracts for CFPS. In other words, reagents can be added to the droplets after expression has occurred.

EWoD devices are known to be limited in industrial utility as they are prone to biofouling resulting in irreversibly pinning of aqueous droplets. For this reason, no digital microfluidic devices have been used to demonstrate the EWoD-based actuation of cell-free protein synthesis reagents. The inventors have achieved EWoD-based CFPS through the use of an oil-filled EWoD device. They have surprisingly demonstrated that CFPS reagents can be actuated on an oil-filled EWoD device for hours with minimal surface fouling or biofouling. Actuation (causing active movement via electrokinesis) during the process of expression may also improve the level of expression over a static system where electrokinesis is not used during the expression process.

The cell-free expression of peptides or proteins can use a cell lysate having the reagents to enable protein expression. Common components of a cell-free reaction include an energy source, a supply of amino acids, cofactors such as magnesium, and the relevant enzymes. A cell extract is obtained by lysing the cell of interest and removing the cell walls, DNA genome, and other debris by centrifugation. The remains are the cell machinery including ribosomes, aminoacyl-tRNA synthetases, translation initiation and elongation factors, nucleases, etc. Once a suitable nucleic acid template is added, the nucleic acid template can be expressed as a peptide or protein using the cell derived expression machinery.

Any particular nucleic acid template can be expressed using the system described herein. Three types of nucleic acid templates used in CFPS include plasmids, linear expression templates (LETs), and mRNA. Plasmids are circular templates, which can be produced either in cells or synthetically. LETs can be made via PCR. While LETs are easier and faster to make, plasmid yields are usually higher in CFPS. mRNA can be produced through in vitro transcription systems. The methods use a single nucleic acid template per droplet. The methods can use multiple droplets having a different nucleic acid template per droplet.

An energy source is an important part of a cell-free reaction. Usually, a separate mixture containing the needed energy source, along with a supply of amino acids, is added to the extract for the reaction. Common sources are phosphoenolpyruvate, acetyl phosphate, and creatine phosphate. The energy source can be replenished during the expression process by adding further reagents to the droplet during the process.

The cell-free extract having the components for protein expression includes everything required for protein expression apart from the nucleic acid template. Thus the term includes all the relevant ribosomes, enzymes, initiation factors, nucleotide monomers, amino acid monomers, metal ions and energy sources. Once the nucleic acid template is added, protein expression is initiated without further reagents being required.

Thus the cell-lysate can be supplemented with additional reagents prior to the template being added. The cell-free extract having the components for protein expression would typically be produced as a bulk reagent or 'master mix' which can be formulated into many identical droplets prior to the distinct template being separately added to separate droplets. Common cell extracts in use today are made from *E. coli* (ECE), rabbit reticulocytes (RRL), wheat germ (WGE), insect cells (ICE) and Yeast *Kluyveromyces* (the D2P system). All of these extracts are commercially available.

Rather than originating from a cell extract, the cell-free system can be assembled from the required reagents. Systems based on reconstituted, purified molecular reagents are commercially available, for example the PURE system for protein production, and can be used as supplied. The PURE system is composed of all the enzymes that are involved in transcription and translation, as well as highly purified 70S ribosomes. The protein synthesis reaction of the PURE system lacks proteases and ribonucleases, which are often present as undesired molecules in cell extracts.

The term digital microfluidic device refers to a device having a two-dimensional array of planar microelectrodes. The term excludes any devices simply having droplets in a flow of oil in a channel. The droplets are moved over the surface by electrokinetic forces by activation of particular electrodes. Upon activation of the electrodes the dielectric layer becomes less hydrophobic, thus causing the droplet to spread onto the surface. A digital microfluidic (DMF) device set-up is known in the art, and depends on the substrates used, the electrodes, the configuration of those electrodes, the use of a dielectric material, the thickness of that dielectric material, the hydrophobic layers, and the applied voltage.

Once the CFPS reagents have been enclosed in the droplets, additional reagents can be supplied by merging the original droplet with a second droplet. The second droplet can carry any desired additional reagents, including for example oxygen or 'power' sources, or test reagents to which it is desired to expose to the expressed protein.

The droplets can be aqueous droplets. The droplets can contain an oil immiscible organic solvent such as for example DMSO. The droplets can be a mixture of water and solvent, providing the droplets do not dissolve into the bulk oil.

The droplets can be in a bulk oil layer. A dry gaseous environment simply dries the bubbles onto the surface during the expression process, leaving comet type smears of dried material by evaporation. Thus the device is filled with liquid for the expression process. Alternatively, the aqueous droplets can be in a humidified gaseous environment. A device filled with air can be sealed and humidified in order to provide an environment that reduces evaporation of CFPS droplets.

The droplets containing the cell-free extract having the components for protein expression will therefore typically be in the oil filled environment before the nucleic acid templates are added to the droplets. The templates can be added by merging droplets on the microfluidic device. Alternatively, the templates can be added to the droplets outside the device and then flowed into the device for the expression process. For example the expression process can be initiated on the device by increasing the temperature. The expression system typically operates optimally at temperatures above standard room temperatures, for example at or above 29° C.

The expression process typically takes many hours. Thus the process should be left for at least 30 minutes or 1 hour, typically at least 2 hours. Expression can be left for at least 12 hours. During the process of expression the droplets should be moved within the device. The moving improves the process by mixing the reagents and ensuring sufficient oxygen is available within the droplet. The moving can be continuous, or can be repeated with intervening periods of non-movement.

Thus the aqueous droplet can be repeatedly moved for at least a period of 30 minutes or one hour whilst the protein is expressed. The aqueous droplet can be repeatedly moved for at least a period of two hours whilst the protein is expressed. The aqueous droplet can be repeatedly moved for at least a period of twelve hours whilst the protein is expressed. The act of moving the droplet allows mixing within the droplet, and allows oxygen or other reagents to be supplied to the droplet. The act of moving improves the level of protein expression over a droplet which remains static.

Digital microfluidics (DMF) refers to a two-dimensional planar surface platform for lab-on-a-chip systems that is based upon the manipulation of microdroplets. Droplets can be dispensed, moved, stored, mixed, reacted, or analyzed on a platform with a set of insulated electrodes. Digital microfluidics can be used together with analytical analysis procedures such as mass spectrometry, colorimetry, electrochemical, and electrochemiluminescense.

The droplet can be moved using any means of electrokinesis. The aqueous droplet can be moved using electrowetting-on-dielectric (EWoD). Electrowetting on a dielectric (EWOD) is a variant of the electrowetting phenomenon that is based on dielectric materials. During EWoD, a droplet of a conducting liquid is placed on a dielectric layer with insulating and hydrophobic properties. Upon activation of the electrodes the dielectric layer becomes less hydrophobic, thus causing the droplet to spread onto the surface.

The electrical signal on the EWoD or optically-activated amorphous silicon (a-Si) EWoD device can be delivered through segmented electrodes, active-matrix thin-film transistors or digital micromirrors. Optically-activated s-Si EWoD devices are well known in the art for actuating droplets (*J. Adhes. Sci. Technol.*, 2012, 26, 1747-1771).

Figure 14:
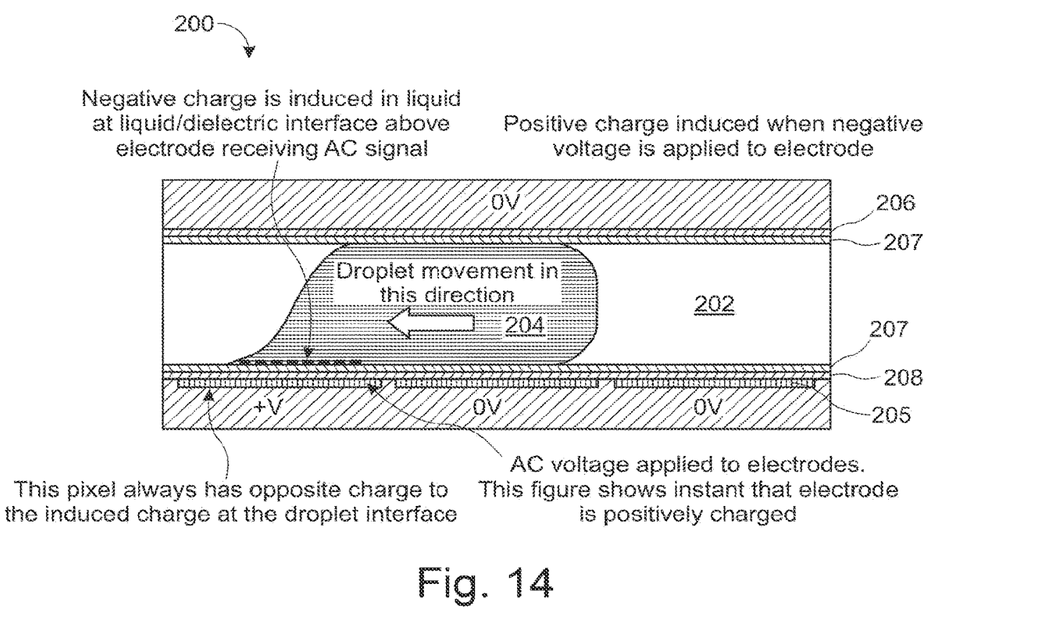
FIG. 14 depicts the movement of an aqueous-phase droplet between adjacent electrodes by providing differing charge states on adjacent electrodes.
Figure 15:
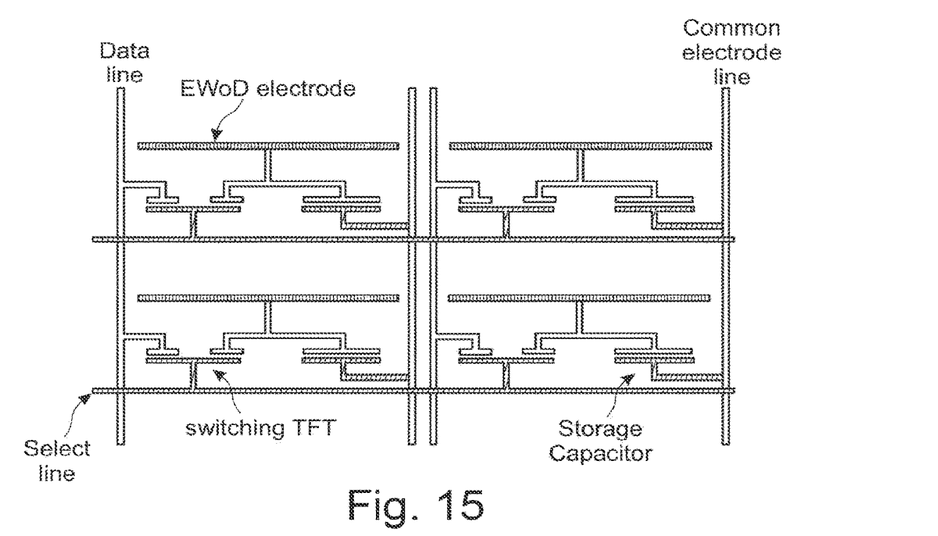
FIG. 15 shows a TFT architecture for a plurality of propulsion electrodes of an EWoD device of the invention.

The present invention includes an active matrix electrowetting on dielectric (AM-EWoD) device including a plurality of thin-film transistors (TFT) to control the electrowetting drive pixels. This configuration may be easily manufactured by modifying the mask patterns customarily used in traditional TFT manufacturing processes, i.e., wherein typically (nearly) all of the pixel electrodes are identical in size and the density of electrodes and drive lines is uniform across the TFT platform. Such TFT arrays are commonplace in liquid crystal displays (LCDs), and often include hundreds of thousands of individually-controllable electrodes. A typical AM-EWoD device consists of a thin film transistor backplane with an exposed array of regularly shaped electrodes which may be arranged as pixels. The pixels may be controllable as an active matrix, thereby allowing for the manipulation of sample droplets. The array is usually coated with a dielectric material, followed by a coating of hydrophobic material. The fundamental operation of a typical EWoD device is illustrated in the sectional image of FIG. 14. The EWoD 200 includes a cell filled with an oil layer (or other hydrophobic fluid) 202 and at least one aqueous droplet 204. The cell gap is typically in the range 50 to 200 µm, but the gap can be larger or smaller. In a basic configuration, as shown in FIG. 14, an array of propulsion electrodes 205 are disposed on one substrate and a singular top electrode 206 is disposed on the opposing surface. The cell additionally includes hydrophobic coatings 207 on the surfaces contacting the oil layer 202, as well as a dielectric layer 208 between the array of propulsion electrodes 205 and the hydrophobic coating 207. (The upper substrate may also include a dielectric layer, but it is not shown in FIG. 14). The hydrophobic coating 207 prevents the droplet from wetting the surface. When no voltage differential is applied between an electrode and the top plate, the droplet will maintain a spheroidal shape to minimize contact with the hydrophobic surfaces (oil and hydrophobic layer). Because the droplets do not wet the surface, they are less likely to contaminate the surface or interact with other droplets except when that behavior is desired. Accordingly, individual aqueous droplets can be manipulated about the active matrix, and mixed, split, combined, as known in the field.

While it is possible to have a single layer for both the dielectric and hydrophobic functions, such layers typically require thick inorganic layers (to prevent pinholes) with resulting low dielectric constants, thereby requiring more than 100V for droplet movement. To achieve low voltage actuation, it is usually better to have a thin inorganic layer for high capacitance and to be pinhole free, topped by a thin organic hydrophobic layer. With this combination it is possible to have electrowetting operation with voltages in the range +/−10 to +/−50V, which is in the range that can be supplied by conventional TFT arrays.

When a voltage differential is applied between adjacent electrodes, the voltage on one electrode attracts opposite charges in the droplet at the dielectric-to-droplet interface, and the droplet moves toward this electrode, as illustrated in FIG. 14. The voltages needed for acceptable droplet propulsion depend on the properties of the dielectric and hydrophobic layers. AC driving is used to reduce degradation of the droplets, dielectrics, and electrodes by various electrochemistries. Operational frequencies for EWoD can be in the range 100 Hz to 1 MHz, but lower frequencies of 1 kHz or lower are preferred for use with TFTs that have limited speed of operation.

As shown in FIG. 14, the top electrode 206 is a single conducting layer normally set to zero volts or a common voltage value (VCOM) to take into account offset voltages on the propulsion electrodes 205 due to capacitive kickback from the TFTs that are used to switch the voltage on the electrodes (see FIG. 15). The use of "top" and "bottom" is merely a convention as the locations of the two electrodes can be switched, and the device can be oriented in a variety of ways, for example, the top and bottom electrode can be roughly parallel while the overall device is oriented so that the substrates are normal to a work surface. The top electrode can also have a positive or negative voltage applied, thereby increasing the voltage across the liquid. This is known as top-plane switching. Such an arrangement allows lower propulsion voltages to be used for the TFT connected propulsion electrodes 205 because the top plate voltage 206 is additional to the voltage supplied by the TFT. Accordingly, it is possible to achieve suitable droplet motion using only ±15V on the pixel electrodes, i.e., a driving voltage that is compatible with microelectronic backplanes fabricated on amorphous silicon.

As illustrated in FIG. 15, an active matrix of propulsion electrodes can be arranged to be driven with data (source) lines and gate (select) lines much like an active matrix in a liquid crystal display. The gate (select) lines are scanned for line-at-a time addressing, while the data (source) lines carry the voltage to be transferred to propulsion electrodes for electrowetting operation. If no movement is needed, or if a droplet is meant to move away from a propulsion electrode, then 0 V will be applied to that (non-target) propulsion electrode. If a droplet is meant to move toward a propulsion electrode, an AC voltage will be applied to that (target) propulsion electrode.

Figure 16:
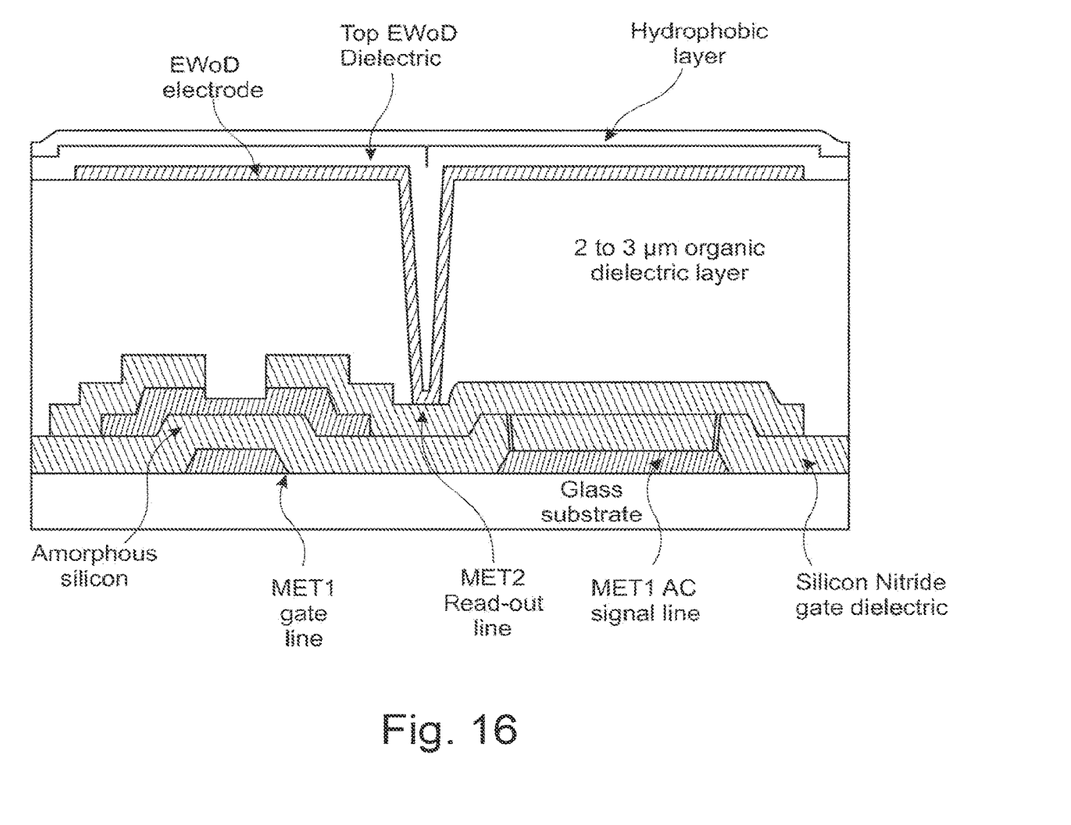
FIG. 16 shows the architecture of an exemplary, TFT-switched, propulsion electrode.

The architecture of an exemplary, TFT-switched, propulsion electrode is shown in FIG. 16. The dielectric should be thin enough and have a dielectric constant compatible with low voltage AC driving, such as available from conventional image controllers for LCD displays. For example, the dielectric layer may comprise a layer of approximately 20-40 nm $SiO_2$ topped over-coated with 200-400 nm plasma-deposited silicon nitride. Alternatively, the dielectric may comprise atomic-layer-deposited $Al_2O_3$ between 5 and 500 nm thick, preferably between 150 and 350 nm thick. The TFT is constructed by creating alternating layers of differently-doped Si structures along with various electrode lines, with methods know to those of skill in the art.

The hydrophobic layer can be constructed from one or a blend of fluoropolymers, such as PTFE (polytetrafluoroethylene), FEP (fluorinated ethylene propylene), PVF (polyvinylfluoride), PVDF (polyvinylidene fluoride), PCTFE (polychlorotrifluoroethylene), PFA (perfluoroalkoxy polymer), FEP (fluorinated ethylene-propylene), ETFE (polyethylenetetrafluoroethylene), and ECTFE (polyethylenechlorotrifluoroethylene). Commercially available fluoropolymers Teflon® AF (Sigma-Aldrich, Milwaukee, WI) and FluoroPel™ coatings from Cytonix (Beltsville, MD), which can be spin coated over the dielectric layer. An advantage of fluoropolymer films is that they can be highly inert and can remain hydrophobic even after exposure to oxidizing treatments such as corona treatment and plasma oxidation. Coatings having higher contact angles may be fabricated from one or more superhydrophobic materials. Contact angles on superhydrophobic materials typically exceed 150°, meaning that only a small percentage of a droplet base is in contact with the surface. This imparts an almost spherical shape to the water droplet. Certain fluorinated silanes, perfluoroalkyls, perfluoropolyethers and RF plasma-formed superhydrophobic materials have found use as coating layers in electrowetting applications and render it relatively easier to slide along the surface. Some types of composite materials are characterized by chemically heterogeneous surfaces where one component provides roughness and the other provides low surface energy so as to produce a coating with superhydrophobic characteristics. Biomimetic superhydrophobic coatings rely on a delicate micro or nano structure for their repellence, but care should be taken as such structures tend to be easily damaged by abrasion or cleaning.

The oil in the device can be any water immiscible or hydrophobic liquid. The oil can be mineral oil, silicone oil, an alkyl-based solvent such as decane or dodecane, or a fluorinated oil. The air in the device can be any humidified gas.

A source of supplemental oxygen can be supplied to the droplets. For example droplets or gas bubbles containing gaseous or dissolved oxygen can be merged with the aqueous droplets during the protein expression. Alternatively the source of oxygen can be a molecular source which releases oxygen. Alternatively the droplets can be moved to an air/liquid boundary to enable increased diffusion of oxygen from a gaseous environment. Alternatively the oil can be oxygenated. Alternatively the droplets can be presented in a humidified air filled device.

The droplet can be formed before entering the microfluidic device and flowed into the device. Alternatively the droplets can be merged on the device. Included is a method comprising merging a first droplet containing a nucleic acid template such as a plasmid with a second droplet containing a cell-free system having the components for protein expression to form the droplet.

The droplets can be split on the device either before, during or after expression. Included herein is a method further comprising splitting the droplet into multiple droplets. If desired the split droplets can be screened with further additives. Included is a method wherein one or more of the split droplets are merged with additive droplets for screening.

Through an affinity tag, such as a FLAG-tag, HIS-tag, GST-tag, MBP-tag, STREP-tag, or other form of affinity tag, CFPS-expressed proteins can be immobilized to a solid-support affinity resin and fresh batches of CFPS reagent can be delivered over the said resin. Thus, renewed reagents can be used to carry out protein synthesis, closely mimicking industrial methods of continuous flow (CF) and continuous exchange (CE) CFPS. By mimicking CF- and CE-CFPS, users can scale up their CFPS production methods.

The droplets can be actuated on a hydrophobic surface on the digital microfluidic device (ACS Nano 2018, 12, 6, 6050-6058). The hydrophobic surface can be a hydrophobic surface such as polytetrafluoroethylene (PTFE), Teflon AF (DuPont Inc), CYTOP (AGC Chemicals Inc), or FluoroPel (Cytonix LLC). The hydrophobic surface may be modified in such a way to reduce biofouling, especially biofouling resulting from exposure to CFPS reagents or nucleic acid reagents. The hydrophobic surface may also be superhydrophobic, such as NeverWet (NeverWet LLC) or Ultra-Ever Dry (Flotech Performance Systems Ltd). Superhydrophobic surfaces prevent biofouling compared with typical fluorocarbon-based hydrophobic surfaces. Superhydrophobic surfaces thus prolong the capability of digital microfluidic devices to move CFPS droplets and general solutions containing biopolymers (RSC Adv., 2017, 7, 49633-49648). The hydrophobic surface can also be a slippery liquid infused porous surface (SLIPS), which can be formed by infusing Krtox-103 oil (DuPont) with porous PTFE film (Lab Chip, 2019, 19, 2275).

Droplets can also contain additives to reduce the effects of biofouling on digital microfluidic surfaces. Specifically, droplets containing CFPS components can also contain additives such as surfactants or detergents to reduce the effects of biofouling on the hydrophobic or superhydrophobic surface of a digital microfluidic device (Langmuir 2011, 27, 13, 8586-8594). Such droplets may use antifouling additives such as TWEEN 20, Triton X-100, and/or Pluronic F127. Specifically, droplets containing CFPS components may contain TWEEN 20 at 0.1% v/v, Triton X-100 at 0.1% v/v, and/or Pluronic F127 at 0.08% w/v.

Detection of proteins synthesized by CFPS on a digital microfluidic device can be performed in many ways that are well known in the art. In one embodiment, synthesized proteins are detectable. In one embodiment, synthesized proteins are detectable by optical, electrical, or thermal means. In one embodiment, synthesized proteins are intrinsically detectable by fluorescence, chemiluminescence, absorbance, or electrical signals. In one embodiment, synthesized proteins are detectable by virtue of a detectable tag, which upon further contact by another entity, allows for detection by fluorescence, luminescence, absorbance, or electrical signals through one or more steps. In one embodiment, synthesized proteins are intrinsically fluorescent by virtue of one or more tryptophan residues. In one embodiment, synthesized proteins are intrinsically fluorescent due to maturation of a chromophore or binding of a ligand, such as green fluorescent protein and its derivatives, red fluorescent protein and its derivatives, FMN-binding fluorescent proteins, and any other fluorescent protein. In one embodiment, synthesized proteins include an N-terminal or C-terminal tag comprised of a fluorescent protein. In one embodiment, synthesized proteins include an N-terminal or C-terminal tag comprised of a chromogenic protein.

In one embodiment, synthesized proteins include an N-terminal or C-terminal tag comprised of a protein that is involved in a reaction that generates a detectable signal, such as through chemiluminescence or fluorescence or absorbance or electrical signals. In one embodiment, synthesized proteins include an N-terminal or C-terminal tag comprising of horseradish peroxidase (HRP), alkaline phosphatase (AP), firefly luciferase, and/or beta-galactosidase. In one embodiment, synthesized proteins are labelled with a detectable moiety, such as maleimide-HRP or maleimide-Cy3. It is well known in the art that HRP, AP, firefly luciferase, or beta-galactosidase can become detectable by exposure to luminol, dihydroxyacetone/lucigenin, luciferin/ATP/oxygen, or ortho-nitrophenyl-D-galactopyranoside, respectively.

In one embodiment, synthesized proteins can be immobilized by virtue of an affinity tag. The subsequent immobilized protein can be detected by a protein dye such as SYPRO™ orange or SYPRO™ ruby. In one embodiment, synthesized protein contain an epitope for detection by means of antibody binding and subsequent detection through chemiluminescence, fluorescence, absorbance, or electrical signals, such as through enzyme-linked immunosorbent assay (ELISA).

In one embodiment the synthesized protein is immobilized or concentrated to a surface and detected by a biosensor based on the phenomena of piezoelectricity, impedance, surface plasmon resonance, or surface acoustic waves. In one embodiment the synthesized protein is immobilized or concentrated to a surface and detected using a field-effect transistor based biosensor.

Included herein are kits for performing the method.

Disclosed herein is a kit for preparing a plurality of peptide or proteins comprising
  a. a digital microfluidic device;
  b. a reagent source to generate a plurality of aqueous droplets containing a cell-free extract system having the components for protein expression; and
  c. an oil or oxygenated oil, optionally mineral oil, silicone oil, an alkyl-based solvent such as decane or dodecane, or a fluorinated oil, which can be optionally oxygenated.

The kits may include other components such as for example a population of different nucleic acid templates.

Materials and Methods

Cell-Free Protein Synthesis (CFPS)

The myTXTL Sigma 70 Master Mix and pTXTL-P70a-mmCherry plasmid were used to express mmCherry red fluorescent protein (reagents obtained from Arbor Bioscience Corp). Expression of mmCherry protein was monitored by virtue of the intrinsic fluorescence of mmCherry using an excitation source at 545 nm and emission detector at 605 nm (filter set from Chroma Technology Corp).

Electrowetting-On-Dielectric (EWoD)

CFPS reagents were introduced via side-porting onto an EWoD device (Sci-Bots Inc). EWoD droplet actuation was performed in a dodecane filler medium at 29° C. Fluorescence was monitored over time as a proxy for mmCherry protein expression, as indicated.

Results and Discussion

We demonstrate that a digital microfluidic platform can be used to express protein through cell-free protein synthesis, otherwise known as in vitro protein synthesis. Cell-free extracts in either crude or purified form can be merged with nucleic acids in DNA or RNA form to effect protein synthesis (see FIG. 1 for a general schematic). We specifically demonstrate that mmCherry protein was expressed through CFPS in a 96-well plate (traditional method, FIG. 2) and on an EWoD device (FIG. 3). FIGS. 4 to 9 demonstrate protein expression on digital microfluidic devices.

Experimental Details for Digital Microfluidic Devices

Adhesion Promotion

Adding 0.5% v/v Silane A-174 to a 1:1 ratio of isopropanol/water and stirring for 30 seconds formed solution 1. Solution 1 was left to stand for at least 2 hours to fully react and was used within 24 hours. Substrates were immersed in the Solution 1 for 30 minutes, while ensuring the flex strips of the TFT arrays were kept dry. Substrates were removed and air dried for 15 minutes and then cleaned in isopropanol for 15-30 seconds with agitation using tweezers. Substrates were dried with an air gun and stored in Teflon box for Parylene C coating within 30 hours.

Parylene Coating

Prepared substrates (silanised and non-silanised) were arranged face up on a rotating stage alongside a clean glass slide within the deposition chamber of a thoroughly clean SCS Labcoter 2 and the chamber is sealed. 50 mg of Parylene C dimer was weighed into a disposable aluminium boat and loaded into the sublimation chamber. The system was sealed and pumped down to 50 milliTorr before liquid nitrogen was added to the cold trap. The system continued to evacuate throughout the deposition process. The sublimation chamber was heated to 175° C. and the heater cycled to maintain a target pressure of 0.1 Torr. The sublimation chamber is connected to the deposition chamber by a pyrolysis zone which was heated to 690° C. at a target pressure of 0.5 Torr. The deposition zone remained at ambient temperature, circa 25° C., and around 50 milliTorr. The system was maintained at temperature and pressure for two hours. The system was allowed to return gradually to ambient temperature over 30-40 minutes before the stage and vacuum pump were turned off and the system vented. The samples were removed from the deposition chamber and the coating thickness verified as circa 100 nm by profilometry.

All digital microfluidic devices used contain dodecane (Sigma Aldrich) as a filler oil. All cell-free protein synthesis reagents consist of the following: myTXTL Sigma 70 Cell-Free Master Mix (Daicel Arbor Biosciences), p70a-mCherry (Daicel Arbor Biosciences), and/or p70a(2)-deGFP (Daicel Arbor Biosciences). All cell-free protein synthesis reagents contain tween-20 (Thermo Fisher Scientific). Interstitial reservoirs were formed by pipetting 1-10 microliters of reagent into the cell-gap of the digital microfluidic device.

Figure 4:
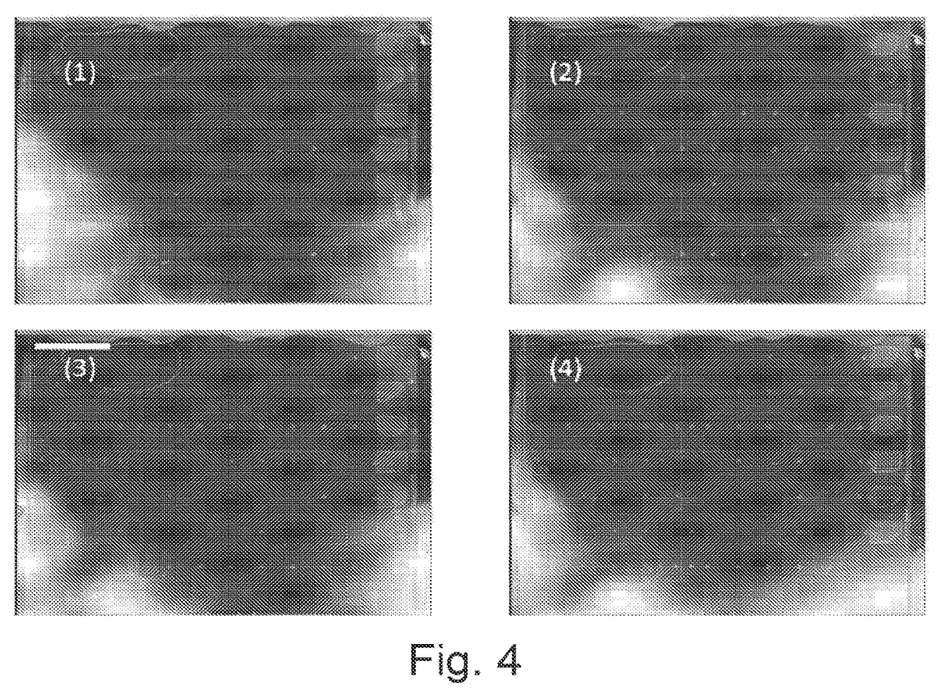
Figure 5:
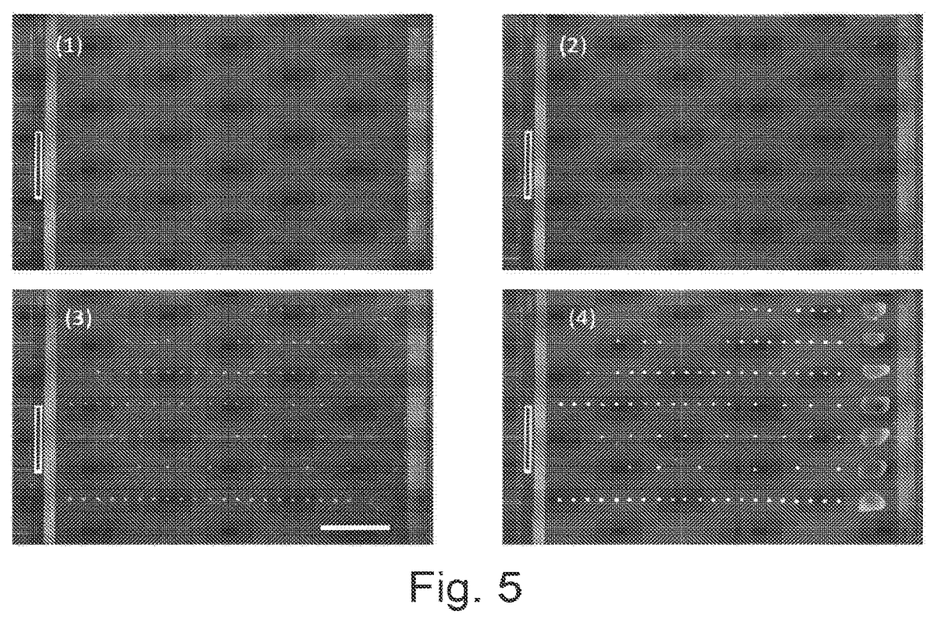
Figure 6:
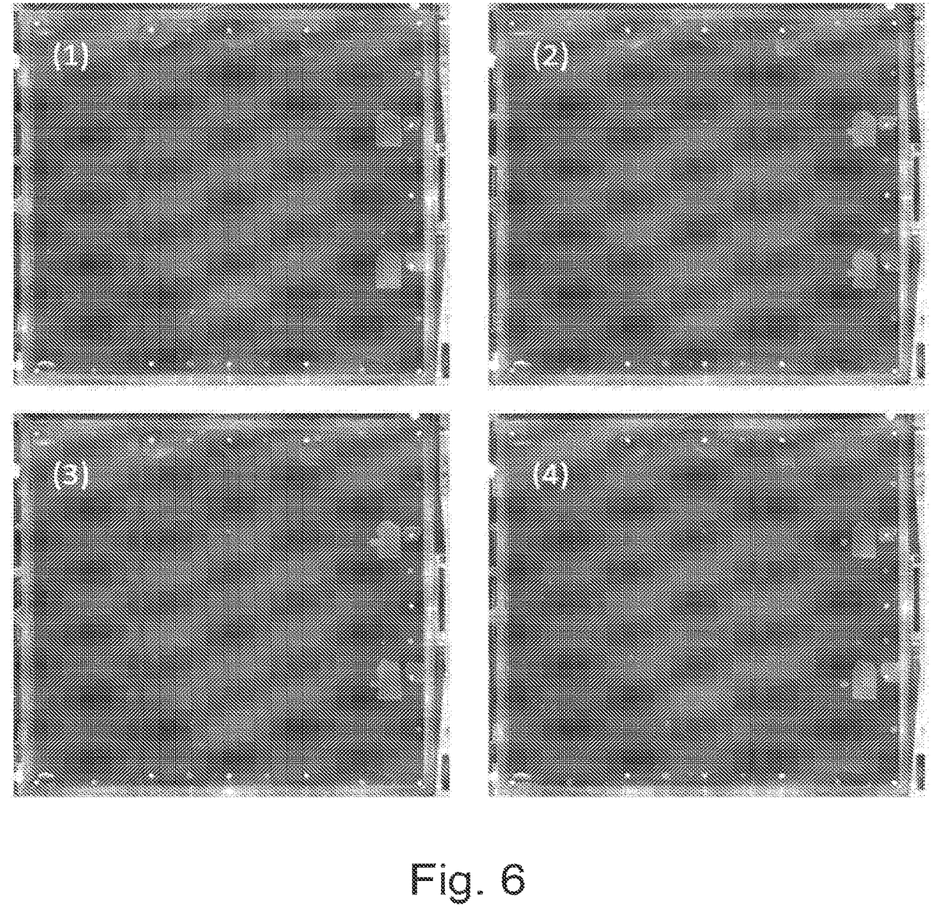
FIG. 6. Moving and splitting droplets containing cell-free protein synthesis reagents on a digital microfluidic device without nucleic acid template pre-mixed. A single droplet was split from interstitial reagent reservoirs (arrows) containing CFPS reagents on an active-matrix EWOD droplet actuator device. The reservoir contains a solution comprising all reagents necessary for cell-free protein synthesis with the exception of a nucleic acid template encoding for a protein of interest. Cell-free protein synthesis reagents contain Tween-20 (0.1% v/v). Droplets of size 1.4 mm$^2$ were requested from the interstitial reagent reservoirs. Video snapshots (1)-(4) move forward in time.
Figure 7:
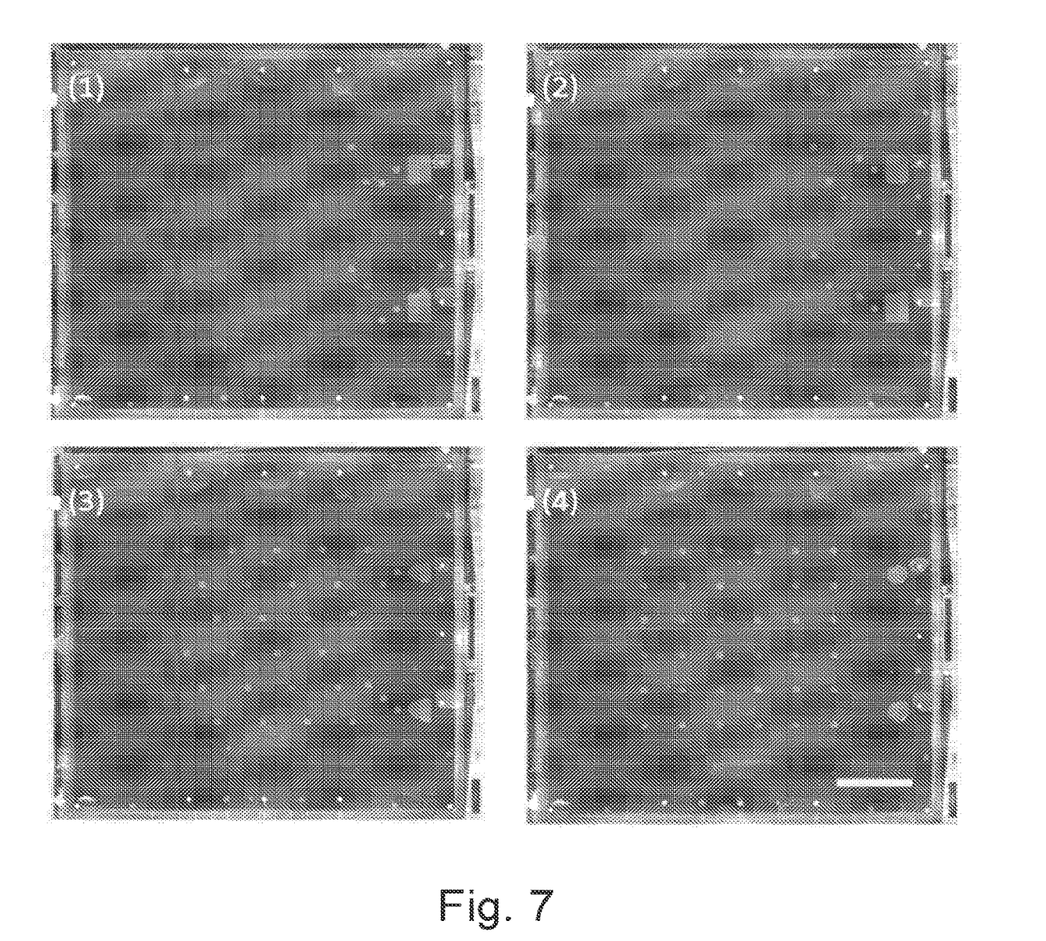
FIG. 7. Setting up a cell-free protein synthesis 6×6 droplet array on a digital microfluidic device without nucleic acid template pre-mixed. Multiple droplets were split from interstitial reagent reservoirs (arrows) containing CFPS reagents on an active-matrix EWOD droplet actuator device to form a 6×6 droplet array (middle of device). The reservoir contains a solution comprising all reagents necessary for cell-free protein synthesis with the exception of a nucleic acid template encoding for a protein of interest. Cell-free protein synthesis reagents contain Tween-20 (0.1% v/v). Droplets of size 1.4 mm$^2$ were requested from the interstitial reservoirs. Video snapshots (1)-(4) move forward in time. Scale bar is 20 mm.
Figure 8:
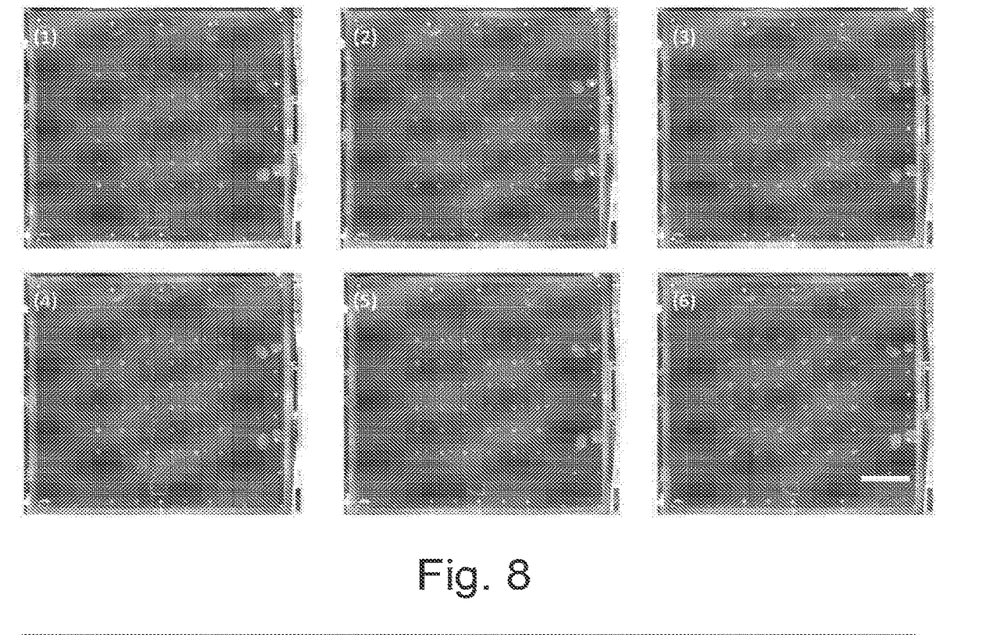
FIG. 8. Initiating cell-free protein synthesis on a digital microfluidic device through the addition of a plasmid droplet. Multiple droplets were split from interstitial reagent reservoirs (arrow) containing plasmid necessary to initiate protein synthesis and subsequently the plasmid droplets were merged and mixed into a previously formed 6×6 CFPS droplet array to initiate protein synthesis on an active-matrix EWOD droplet actuator device. The interstitial reservoirs contain a solution comprising a nucleic acid template in the form of a plasmid encoding for a protein of interest necessary to initiate protein synthesis in the previously formed 6×6 CFPS droplet array in the middle of the device. The protein of interest here is deGFP. Cell-free protein synthesis reagents contain Tween-20 (0.1% v/v). Droplets of size 1.4 mm$^2$ were requested from the interstitial reagent reservoirs. Video snapshots (1)-(6) move forward in time. Snapshots (1)-(4) show droplet splitting and actuation of plasmid droplets. Snapshots (5)-(6) show merging and mixing of the plasmid droplets with a previously formed 6×6 droplet array of CFPS reagents. After snapshot (6), protein synthesis is initiated. Scale bar is 20 mm.
Figure 9:
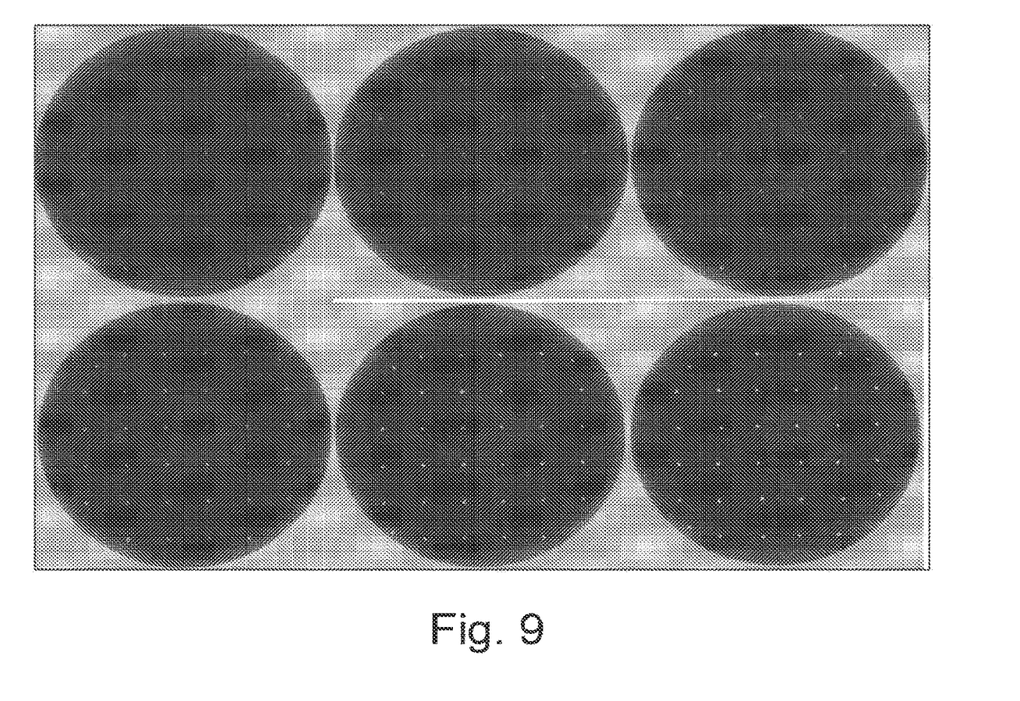
FIG. 9. Expression of deGFP fluorescent protein through cell-free protein synthesis on a digital microfluidic device. The 6×6 droplet array comprised of 0.6 mm$^2$ droplets containing all necessary reagents for deGFP fluorescent protein via cell-free protein synthesis was formed in the same fashion as the figures above. Snapshots show deGFP cell-free protein synthesis over 24 hours at 26° C.; snapshots move forward in time from top row, left to right and bottom row, left to right. Image acquisition time was 900 milliseconds. Images were acquired with a camera (Basler ACE) using a RICOH 9M 12 mm lens and a 605/70 nm emission filter. A RM140BL ring light was used directly as the excitation source.
Figure 10:
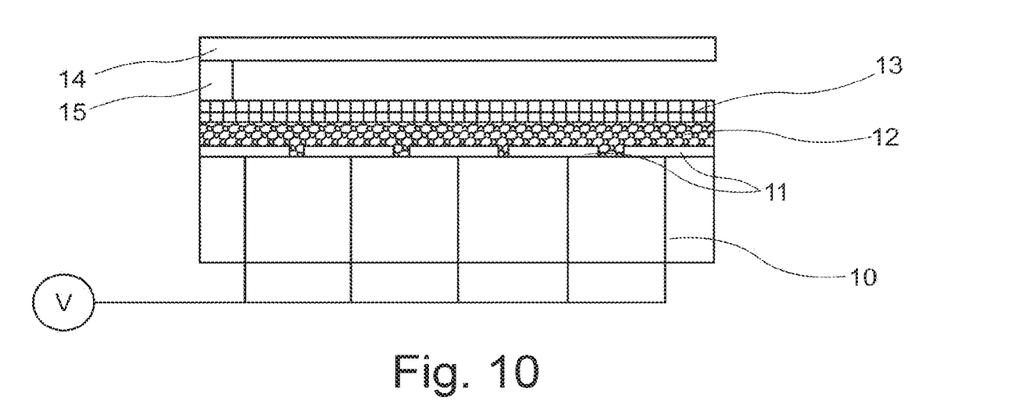
FIG. 10 shows cross sectional schematic for a traditional EWoD device.
Figure 11:
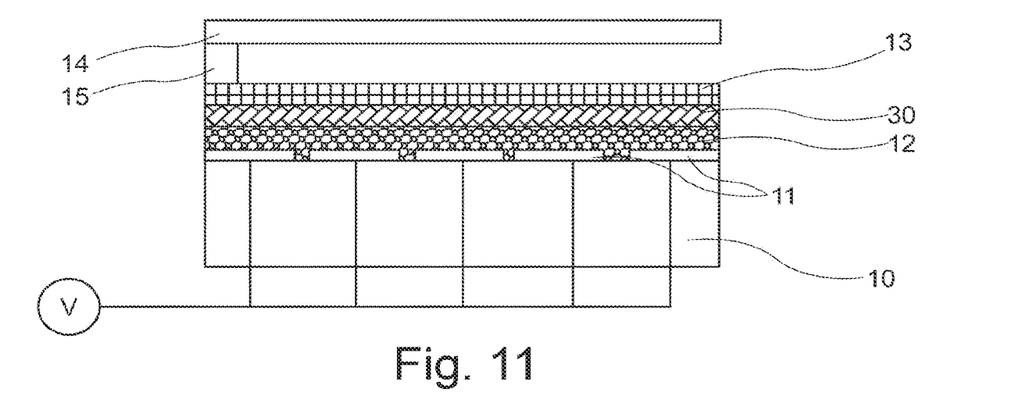
FIG. 11 shows a cross section of a device according to the invention.
Figure 12:
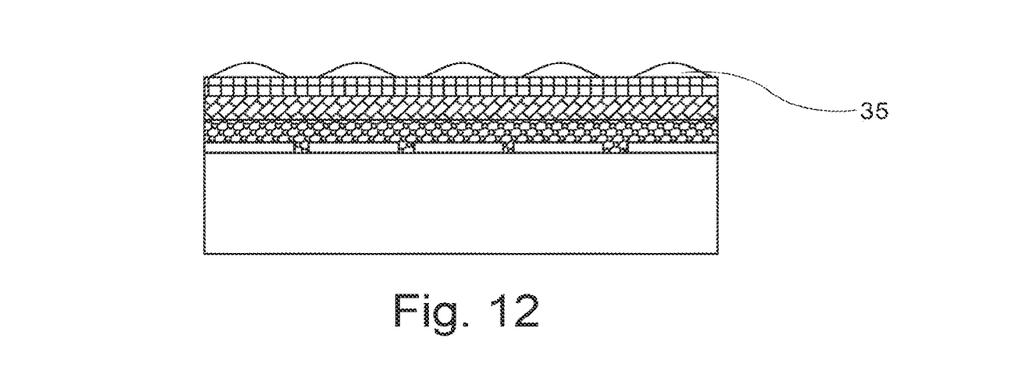
FIG. 12 depicts a device according to the invention with voltages applied and droplets. Through the application of a voltage the aqueous solution forms droplets 35 above the individually controllable elements.
Figure 13:
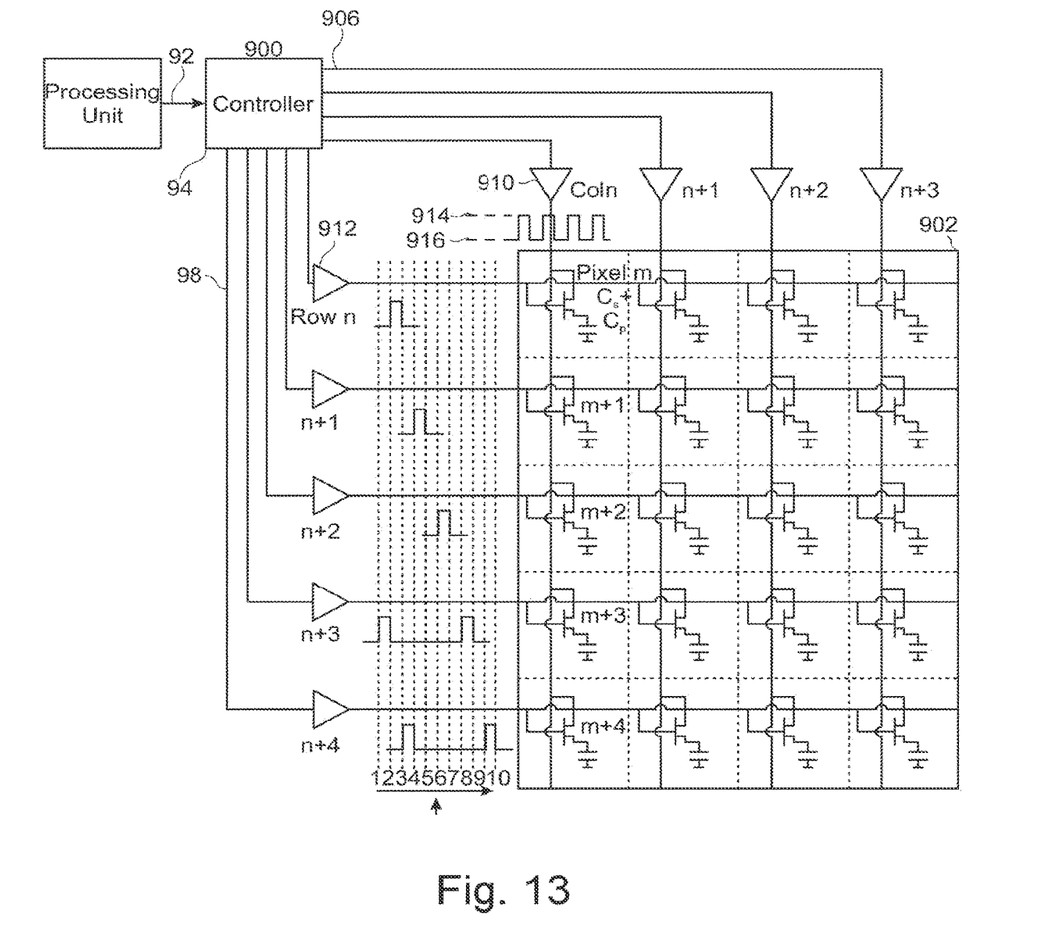
FIG. 13 depicts an active matrix as used in conjunction with the invention.

For FIGS. 4-5, images were acquired as described in FIG. 3. For FIG. 9, images were acquired with a camera (Basler ACE) using a RICOH 9M 12 mm lens and a 605/70 nm emission filter. A RM140BL ring light was used directly as the excitation source.

CONCLUSION

Figure 1:
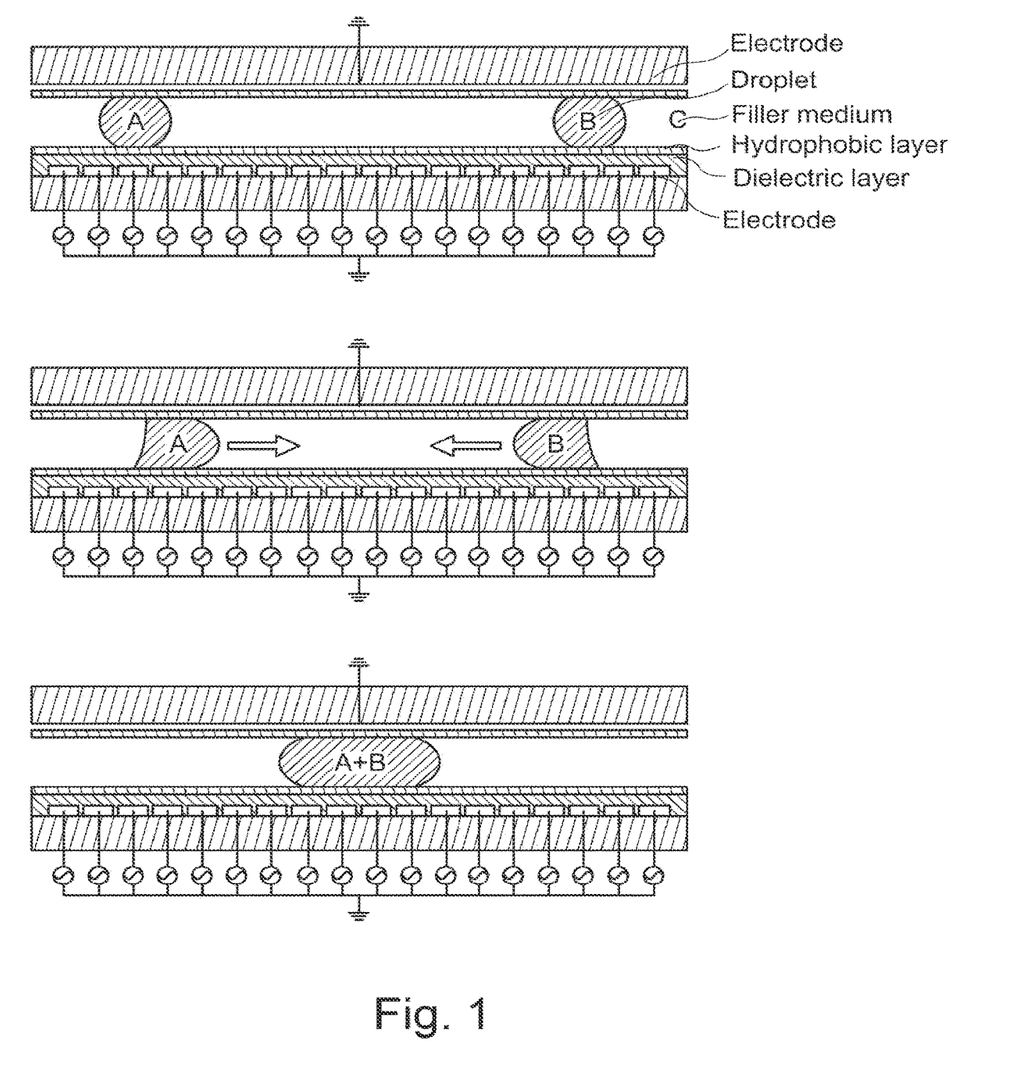
Figure 2:
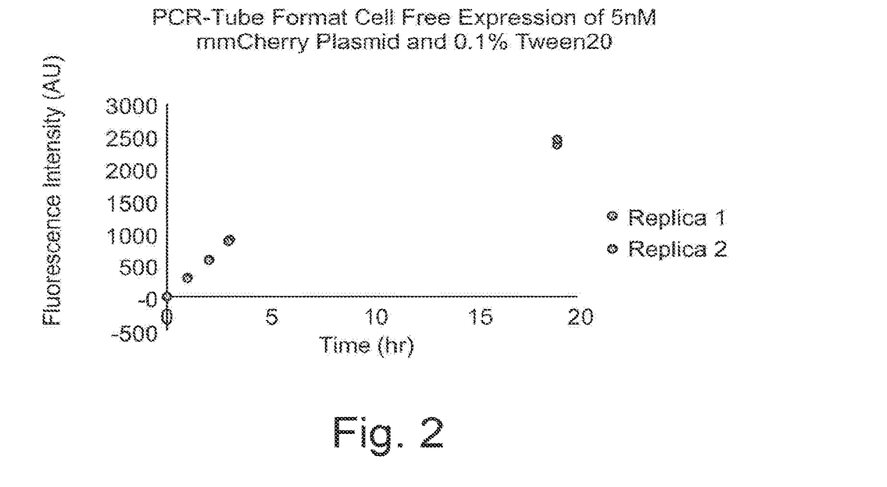
Figure 3:
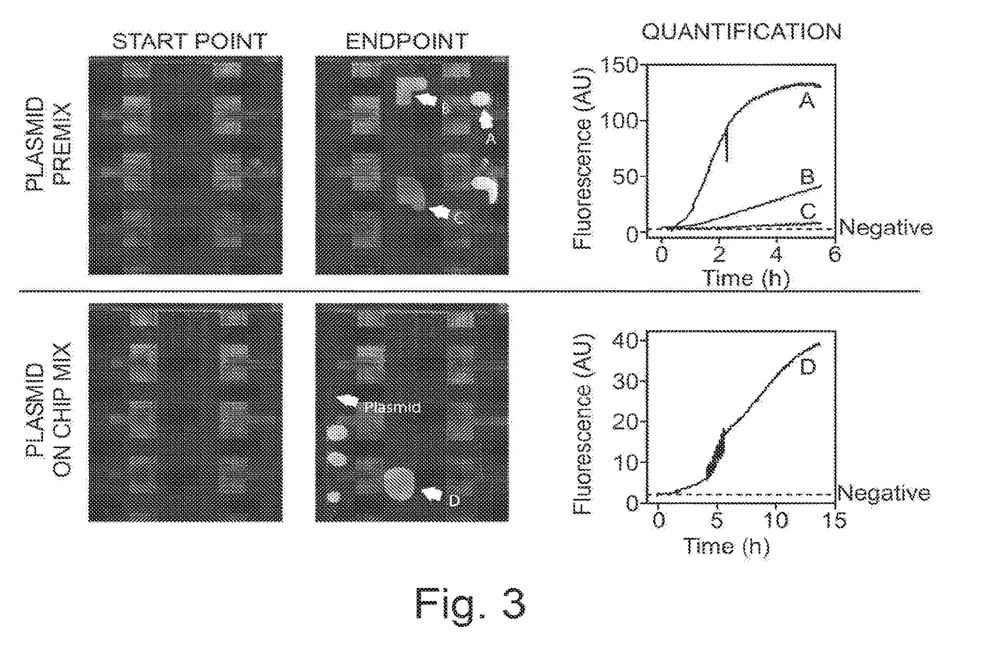

FIGS. 1-3 demonstrate that CFPS reagents can be moved by electrokinetic processes to effect CFPS on an EWoD device. FIG. 3 (bottom) demonstrates that a separate plasmid droplet can be merged via EWoD actuation into a cell-free extract, and the combined droplet can be electrically actuated and mixed for hours to effect CFPS. This long-term actuation of CFPS droplets is surprising as it is well-known in the art that EWoD devices are sensitive to a type of surface fouling known as bio-fouling, which prevents EWoD actuation. We attribute the ability to actuate CFPS droplets to the use of oil as a filler medium rather than atmospheric air. FIGS. 4 to 9 demonstrate protein expression on digital microfluidic devices.

The invention claimed is:

1. A method for the cell-free expression of proteins in a digital microfluidic device having a two-dimensional array of planar microelectrodes and having an oil-filled environment or a sealed humidified gaseous environment, the method comprising:
  a. taking a plurality of nucleic acid droplets having a different nucleic acid template,
  b. taking a plurality of cell-free expression system droplets, each containing a cell-free system having components for protein expression, c. combining the droplets of a. and b. using electrowetting-on-dielectric (EWoD) to produce a plurality of protein expression droplets capable of expressing proteins, d. mixing the protein expression droplets for a period of at least 2 hours to enable cell-free expression of synthesized proteins that include a detectable tag, and e. merging the protein expression droplets with additive droplets having an entity which binds to the detectable tag to form a fluorescent protein, in order to screen protein expression levels by measuring fluorescence from the fluorescent protein; thereby detecting the expression of proteins within individual droplets.

2. The method according to claim 1 wherein the droplets are repeatedly moved with intervening periods of non-movement for the period of at least 2 hours whilst cell-free protein expression is occurring.

3. The method according to claim 1 wherein the digital microfluidic device has said sealed humidified gaseous environment, and wherein said sealed humidified gaseous environment is achieved by enclosing or sealing the digital microfluidic device and providing on-board reagent reservoirs.

4. The method according to claim 1 wherein the electrical signal on the EWoD or optical EWoD device is delivered through segmented electrodes, active-matrix thin-film transistors, or digital micromirrors.

5. The method according to claim 1 wherein oil in the oil-filled environment is mineral oil, silicone oil, an alkyl-based solvent including decane or dodecane, or a fluorinated oil.

6. The method according to claim 1 wherein oil in the oil-filled environment is oxygenated.

7. The method according to claim 1 wherein a source of supplemental oxygen is supplied to the protein expression droplets.

8. The method according to claim 1, wherein the temperature is maintained at or above 19° C.

9. The method according to claim 1 wherein the cell-free system is a cell-free extract for protein expression.

10. The method according to claim 1 wherein the cell-free system is prepared from individual reagents.

11. The method according to claim 1 further comprising splitting the protein expression droplets into multiple protein expression droplets.

12. The method according to claim 3 wherein the sealed humidified gaseous environment is humidified air.

13. The method according to claim 1, wherein the fluorescent protein is green fluorescent protein (GFP).

* * * * *